United States Patent

Barnea et al.

[11] Patent Number: 5,981,198
[45] Date of Patent: *Nov. 9, 1999

[54] PREIMPLANTATION FACTOR

[76] Inventors: Eytan R. Barnea, 1697 Lark La., Cherry Hill, N.J. 08003; Carolyn B. Coulam, 11015 Bryar Lynn Ct., Fairfax Sta., Va. 22039

[*] Notice: This patent issued on a continued prosecution application filed under 37 CFR 1.53(d), and is subject to the twenty year patent term provisions of 35 U.S.C. 154(a)(2).

This patent is subject to a terminal disclaimer.

[21] Appl. No.: 08/777,911

[22] Filed: Dec. 23, 1996

Related U.S. Application Data

[62] Division of application No. 08/216,618, Mar. 23, 1994, Pat. No. 5,646,003.

[51] Int. Cl.$^6$ .................................................. G01N 33/53
[52] U.S. Cl. .................... 435/7.23; 435/7.24; 435/806; 436/506; 436/501; 436/510
[58] Field of Search ................................ 435/7.23, 7.24, 435/806; 436/506, 501, 510

[56] References Cited

U.S. PATENT DOCUMENTS 5,646,003  7/1997  Barnea et al. .......................... 435/7.24

OTHER PUBLICATIONS

Bose, et al., *Am. J. Obstet. Gynecol.*, vol. 160, No. 4, pp. 954–960, 1989 (abstract only).
Clarke, et al., *Reprod. Fertil. Dev.*, vol. 4, No. 4, pp. 423–433, 1992 (abstract only).
Clarke, et al., *J. Reprod. Fertil.*, vol. 93, No. 2, pp. 525–539, 1991, (abstract only).
Coulam, 1992, Am. J. Reprod. Immunol. 27:130–135.
Battye et al., 1991, J. Reprod. Fertil. 93:507–514.
Bose et al., 1991, Immunol. Letts. 30:325–333.
Clarke et al., 1991, J. Reprod. Fertil. 93:525–539.
Nahas and Barnea, 1990, J. Reprod. Immunol. 22:105–108.
Bose et al., 1989, Am. J. Obstet. Gynecol. 160:954–996.
Sanyal et al., 1989, Am. J. Obstet. Gynecol. 161:446–453.
May, 1988, "Infertility. Medical and Social Choices" U.S. Congress, Office of Technology Assessment. DTA BA 358. U.S. Government Printing Office, Washington, D.C.
Collier et al., 1988, Hum. Reprod. 3:993–998.
O'Neill et al., 1988, Ann. NY Acad. Sci. 541:398–403.
Chard and Grudzinska, 1987, Biol. Res. in Pregnancy 8:53–56.
Mosher and Pratt, 1987, "Fecundity, Infertility and Reproductive Health in the United States, 1992", Vital and Health Statistics, Series 23, No. 14, National Center for Health Statistics, Public Health Service, U.S. Government Printing Office, Washington, D.C. 27.
O'Neill et al., 1987, Fertil. Steril. 47:967–975.
Quin and Zheng, 1987, Am. J. Reprod. Immunol. Microbiol. 13:15–19.
Hanahan, 1986, Ann. Rev. Biochem. 483–509.
O'Neill, 1985, J. Reprod. Fertil. 75:375–380.
O'Neill, 1985, J. Reprod. Fertil. 73:559–564.
Smart et al., 1985, in "Early Pregnancy Factors", Ellendorf and Koch, eds., Perinatology Press, Ithaca, NY, pp. 105–116.
Chen et al., 1984, Ann. NY Acad. Sci. 442:420–424.
Tinneberg et al., 1984, Am. J. Reprod. Immunol. 5:151–155.
Whyte and Heap, 1983, Nature 304:121–122.
Rolfe, 1982, Fertil. Steril. 37:655–701.
Smart et al., 1982, Fertil. Steril. 37:779–785.
Smart et al., 1982, Clin. Reprod. Fertil. 1:177–182.
Templeton and Penny, 1982, Fertil. Steril. 37:175.
Cooper and Aitken, 1981, J. Reprod. Fertil. 61:241–244.
Smart et al., 1981, Fertil. Steril. 35:397–403.
Thomson et al., 1980, J. Reprod. Immunol. 2:263–266.
Morton et al. 1977, Lancet 1:394–399.
Morton et al., 1976, Proc. R. Soc. London 193:413–417.

*Primary Examiner*—Paula Hutzell
*Assistant Examiner*—Nancy Johnson
*Attorney, Agent, or Firm*—Baker & Botts, LLP; Richard S. Clark

[57] ABSTRACT

A factor that indicates fertilization of an ovum before implantation, Preimplantation Factor (PIF), has been found. PIF also provides an early indication of pregnancy, malignancy, and autoimmune diseases. Assays for PIF are described. Detection of PIF in mammalian blood and other fluids is utilized in various diagnostic tests.

9 Claims, 2 Drawing Sheets

PREIMPLANTATION FACTOR

This is a divisional of application Ser. No. 08/216,618 filed on Mar. 23, 1994, now U.S. Pat. No. 5,646,003.

BACKGROUND OF THE INVENTION

Infertility is a major health care concern affecting millions of couples worldwide, including approximately five million in the United States (5). Diagnosis and treatment of infertility are costly. About one million couples have no discernable cause for their infertility (7). Reproductive life table analysis indicates that the majority of reproductive failures occur immediately after fertilization during the preimplantation period (8).

It is important to be able to identify infertile individuals experiencing recurrent post fertilization failures. Identification of such individuals would allow more focused investigations for specific treatment of recurrent post fertilization failure. Exclusion of these individuals from treatment programs designed to enhance fertilization rather than implantation would decrease the cost of infertility therapy by eliminating inefficient treatments.

After fertilization the developing human preembryo takes approximately six days to traverse the oviduct, enter the uterine cavity and implant in the maternal endometrium. Implantation of the embryo, rather than fertilization, is the rate limiting process in human reproduction differentiating fertile from nonfertile cycles. Yet in the human female the events occurring between ovulation and implantation in vivo are clinically silent. A marker for fertilization before implantation was sought.

Two factors have been reported as markers of fertilization in women—embryo derived platelet activating factor (EPAF) (9–12) and early pregnancy factor (EPF) (1,2, 13–17). PAF (platelet activating factor) is a potent phospholipid mediator which is produced by many cell types and has recently been implicated in numerous reproductive processes (18). EPAF production has been documented in murine, ovine and human preembryos (9,19,20). In human in vitro fertilization (IVF) embryos, increased PAF production has been related to a higher probability of clinical pregnancy (10). EPAF appears to be identical to PAF, and therefore cannot be used as a marker of fertilization in vivo since maternal serum concentrations of PAF are higher than that contributed by the embryo.

Early pregnancy factor (EPF) was first described as a pregnancy associated factor in 1976 (3). Since that time, EPF has been detected in sera from women within 24–48 hours of fertilization (1,2,13–17,21,22) or within three days of embryo transfer (14). Assays for EPF have subsequently been applied to a number of clinical situations in the woman including detection of early pregnancy failure following fertilization in normal women (1,2,13–17,21), in women with an intrauterine device (12) and in women undergoing embryo transfer (14). Even so, the measurement of EPF has not been applied to the care of patients.

Lack of clinical application of EPF into reproductive medicine can be attributed to the assay used to detect EPF. EPF has been detected by a bioassay using sheep red blood cells known as the rosette inhibition assay (RIT) (3). The RIT is complex and technically difficult to perform. Results from the RIT are semiquantitative, variable and not always reproducible (23,24). Some authors have completely failed to reproduce the phenomenon (25,26).

SUMMARY OF THE INVENTION

We have found a previously unknown Preimplantation Factor (PIF) in maternal serum. This factor appears promptly after fertilization of an ovum has occurred, before the fertilized ovum becomes implanted, and continues during pregnancy. We have developed a novel bioassay, the lymphocyte/platelet binding assay, for PIF in blood or other bodily fluids such as urine, saliva, tears and/or media used to culture in vitro fertilized ova. Development of other assays such as ELISA and other immunoassays and chemolucent assays for PIF are made possible by use of the bioassay as standard. Known immunoassay techniques are employed to determine the presence or absence of PIF in blood by contacting with monoclonal antibodies to PIF and determining the amount of PIF, if any, that becomes bound to a fixed quantity of antibody. Isolation and identification of proteins constituting PIF, made possible by use of PIF assay permits their application to development of diagnostic and therapeutic tools.

Early pregnancy factor (EPF) binds to lymphocytes and decreases rosette formation in the sheep red blood cell inhibition assay (RIT) (3). By contrast, in our assay PIF enhances lymphocyte binding to platelets demonstrating the ability of PIF to cause enhanced platelet-lymphocyte interactions. Whatever the mechanisms of action, PIF can be measured in our bioassay by virtue of its enhancement of interaction between platelets and lymphocytes. This phenomenon is pregnancy specific, and is not the result of actions of pregnancy hormones such as progesterone or human chorionic gonadotropin (hCG).

Until now, the major limitation in applying the measurement of an early pregnancy factor as a clinical tool has been the difficulty and lack of reproducibility of results obtained when using other assays. Our new lymphocyte/platelet binding assay which detects PIF is easy (4 reagents), reproducible (intra-and interassay variabilities of less than 3%) and cost efficient (time for each assay is less than 5 minutes). Application of this assay allows identification and monitoring of early pre-embryo and embryo viability, events heretofore clinically silent, and allows improved management of early pregnancy.

Our bioassay for PIF is essentially 100% sensitive and 100% specific in retrospective study. It has high predictive power; the presence of PIF confidently predicts pregnancy just 4 days or earlier after intercourse, and this before implantation as opposed to the available test for human chorionic gonadotropin (hCG) which shows whether there is pregnancy only at day 11. This information is very important to the physician dealing with fertility, as it tells her/him definitely whether fertilization of the ovum has taken place.

In a contraception regimen, positive early knowledge that fertilization has occurred permits the administration of an agent that negates implantation, thereby eliminating the need for abortion to terminate unwanted pregnancies. Such anti-implantation agents include antibodies to hCG, anti-progesterones such as RU-486, high doses of estrogen and antibodies to PIF.

PIF remains positive throughout at least the first trimester of pregnancy. Thus, our assay provides a convenient pregnancy test.

We have also found that the assay predicts spontaneous loss of pregnancies. PIF becomes negative about two weeks prior to clinical demonstration of intrauterine demise at the time hCG concentrations remained elevated.

A valuable utility of our assay derives from the fact that PIF is a pregnancy marker in all mammals. No such universal animal pregnancy test is currently available. Thus, the assay can be used to detect pregnancy or lack of it in domestic and zoologic animals and endangered species.

Our ability to assay for PIF is useful in cancer detection and treatment. There is a striking parallel between pregnancy and cancer. A fertilized ovum is a new entity in the body, and requires a forgiving immune system that will allow it to exist and proliferate. So, too, with an initial cancer cell. Each must initiate and maintain an immunosuppressive system to ensure its own defense against immunological rejection. As with fertilized ova, cancer cells produce PIF. Hence, a positive assay of serum or other body fluid showing the presence of PIF may indicate in the non-pregnant mammal the early presence of malignancy. The assay is also useful in following the progress of cancer therapies. Further, monoclonal antibodies to PIF can be used to inhibit the growth of malignant tumors.

The immunosuppressive action of PIF is indicated by the binding of platelets to lymphocytes. Patients suffering from immune system disorders, especially autoimmune diseases, may show a positive titre of PIF in their body fluids, enhancing the diagnosis and treatment of the disease.

IN THE DRAWINGS

FIG. 1: Scattergram of PIF activity measured in serum samples from pregnant and non-pregnant subjects. % binding=number of lymphocytes binding to platelets/number of lymphocytes binding to platelets plus free lymphocytes×100. Mean binding±standard deviation is 63%±10% among pregnant women and 23%±6% among non-pregnant individuals (p<0.001).

FIG. 2: Microphotograph showing results of lymphocyte/platelet binding assay using sera from non-pregnant (FIG. 2A) and pregnant (FIG. 2B) individuals. Low % binding of platelets to lymphocytes is seen when serum from a non-pregnant subject is used in the assay (A) and high % binding is noted when serum from a pregnant woman is used (B).

DETAILED DESCRIPTION

Figure 1:
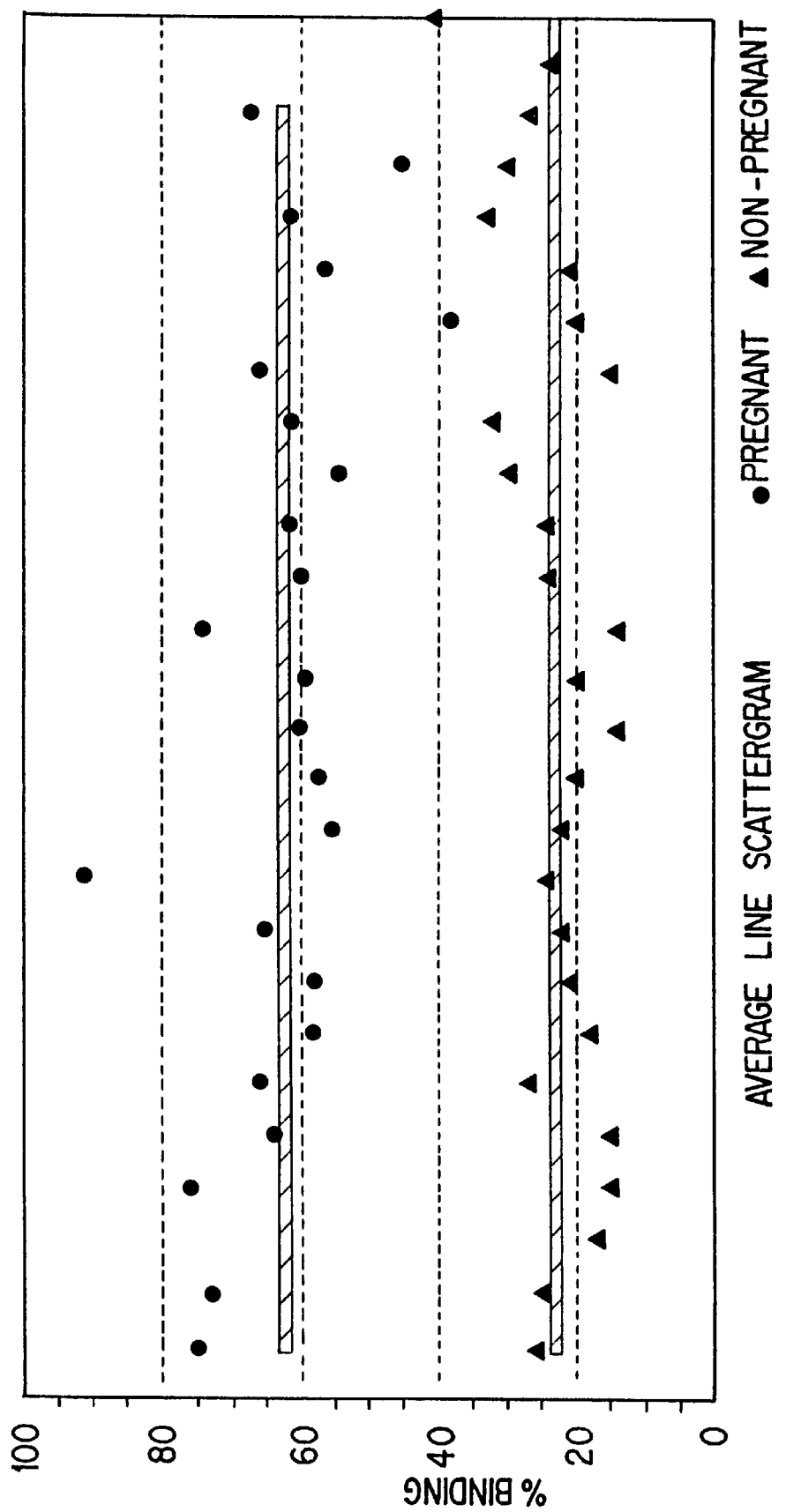

Materials and Methods
Patient Population

In a retrospective study, serum samples from 60 human individuals (including 10 males, 20 non-pregnant females and 30 pregnant females) were analyzed in the lymphocyte/platelet binding assay. Blood was drawn at various times throughout the menstrual cycle, and at different times after transfer of in vitro embryos. Three non-pregnant women received progesterone replacement therapy, and one was taking oral contraceptive pills containing estrogen and progesterone.

Chemicals

Guinea pig complement (GPC), Histopaque and Dulbecco's Phosphate Buffered Saline (PBS) were obtained from Sigma (St. Louis, Mo.). T-11 monoclonal antibody which recognizes the CD2 receptor on the lymphocytes was obtained from Ortho Pharmaceuticals (Raritan, N.J.). One can advantageously use other reagents, for example, rabbit complement (Sigma), T-11 antibody (Dakko, Denmark).

Preparation of Lymphocytes

Eight ml of blood from a healthy O+ donor was diluted 1:1 with PBS and was layered over 12 ml of Histopaque column in a 50 ml test tube and centrifuged at 2400 rpm for 20 minutes to isolate lymphocytes plus platelets by density gradient. Following centrifugation the buffy coat was removed, diluted 1:1 with PBS and washed twice with PBS at 1100 rpm for 10 minutes each time removing the supernatant. During each washing process 2 ml of double distilled water was added to lyse the residual red blood cells. The lymphocytes and platelets recovered were diluted in PBS to $10^{12}$ cells per ml.

Lymphocyte/Platelet Binding Assay

The lymphocyte/platelet binding assay was carried out in microcentrifuge tubes in a total volume of 60 $\mu$l. Assay mixture consisted of 15 $\mu$l of O+ lymphocytes plus platelets, 15 $\mu$l heat inactivated serum of the test subject, 15 $\mu$l activated guinea pig complement, and 15 $\mu$l T11 antibody (anti CD2). Following gentle mixing for 5 minutes 10 $\mu$l of the sample was withdrawn and placed on a slide with a cover slip. The number of lymphocytes with or without bound platelets were counted. A total of 200 cells in three different fields were counted. Samples then were recounted by placing another 10 $\mu$l of mixture on a slide and the average of the duplicate measurements was reported.

Criteria for Evaluating Platelet Binding to Lymphocytes

All lymphocytes were counted at ×400 magnification using a Nikon inverted microscope and were categorized as bound (even if one platelet was bound to the surface) or free if no platelet binding was observed.

Data Analysis

Data are expressed as % platelets-bound lymphocytes per total bound and non-bound lymphocytes. Statistical analysis was carried out by using chi-square analysis with Fischers Exact Test and ANOVA one way analysis of variance. A difference of $P < 0.05$ was considered significant.

Results

FIG. 1 is a scattergram of PIF activity (% platelet binding to lymphocytes) in pregnant women with intact ovaries and subsequent viable pregnancy and in non-pregnant subjects. The percentage of lymphocytes bound by platelets is 63%±10% (mean±SD) among pregnant women and 23%±6% in non-pregnant individuals. The difference between serum samples taken from pregnant and non-pregnant women is significant (p<0.001). Pooled pregnancy sera (N=10) had 59% lymphocytes bound to platelets (data not shown). Intra and interassay variabilities were each less than 3%.

Table I compares the percentage of lymphocyte binding in the PIF assay with the clinical characteristics of the 60 subjects studied. No differences in percentage binding were observed when nonpregnant females in follicular phase of the menstrual cycle were compared with the luteal phase. All male and non-pregnant females had less than 33% binding. Using these values as the non-pregnant controls, 2 standard deviations from the mean is less than 35% binding. Therefore, a test was considered positive when the percentage of lymphocytes bound to platelets was greater than 35%. Five women who underwent in vitro fertilization/embryo transplants and had successful pregnancies had blood drawn serially: the day of embryo transfer, 4 days after embryo transfer when hCG concentrations were negative, and 11 days after embryo transfer when hCG was positive. PIF activity became detectable in the sera in all women by 4 days after embryo transfer.

TABLE I

Percentage of lymphocyte binding in 30 pregnant and 30 nonpregnant individuals

| | | % binding | | | |
|---|---|---|---|---|---|
| | n | mean | SD | SEM | 95% CI |
| Nonpregnant | 30 | 21.2 | 5.9 | 1.0 | 19.2–23.3 |
| Females | 20 | 23.6 | 5.5 | 1.2 | 21.0–26.1 |
| Follicular | 10 | 22 | 4.6 | 1.5 | 18.7–25.3 |
| Luteal | 10 | 25.5 | 6.1 | 1.9 | 20.7–29.5 |
| Males | 10 | 17.7 | 4.7 | 1.3 | 14.8–20.5 |

TABLE I-continued

Percentage of lymphocyte binding in 30 pregnant
and 30 nonpregnant individuals

% binding

|  | n | mean | SD | SEM | 95% CI |
|---|---|---|---|---|---|
| Pregnant | 30 | 56.1 | 15.9 | 2.9 | 50.2–62.0 |

Fol vs Lut NS .2
♀ vs ♂ p = 0.007
Fol vs ♂ p = 0.05
Lut vs ♂ p = 0.007
Preg vs NP = p <0.0001
Preg vs ♀ p <0.0001

Figure 2A:
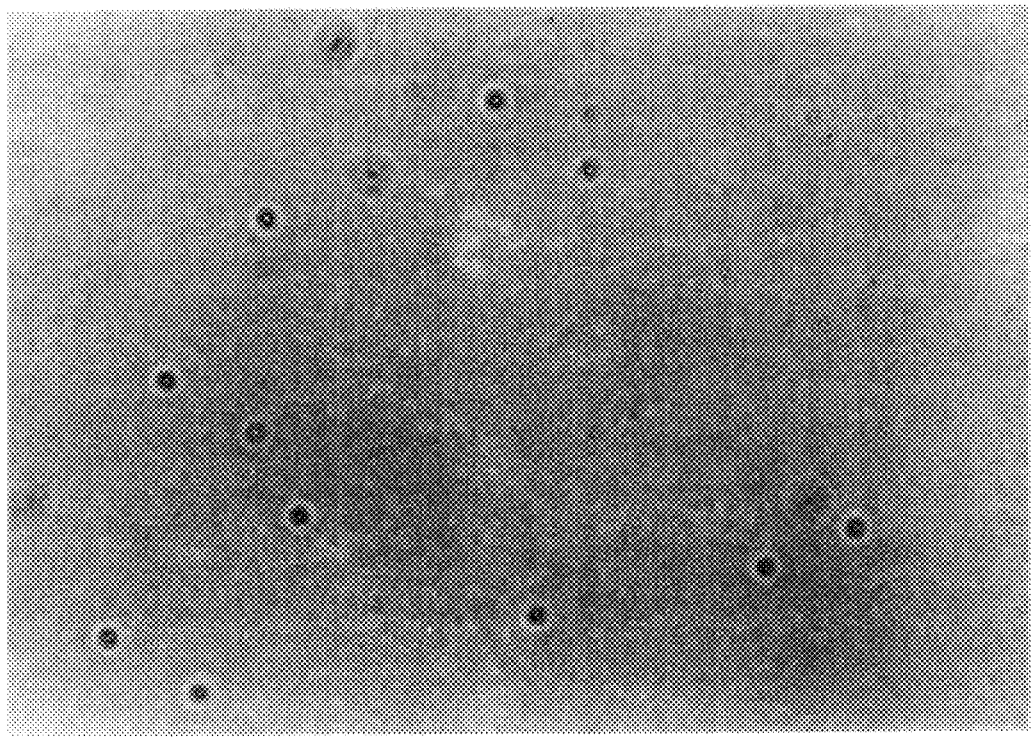
Figure 2B:
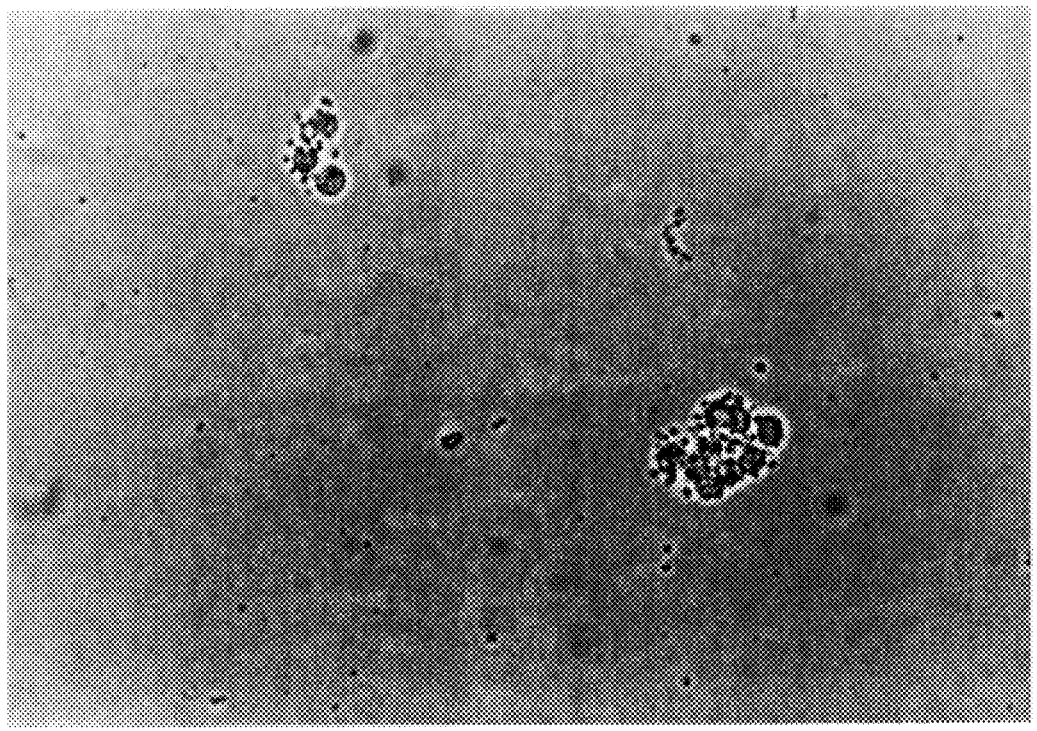

FIG. 2 is microphotograph showing results of platelet binding to lymphocytes using sera from non-pregnant and pregnant women. Low percentage of binding of serum lymphocytes to platelets is seen when serum from a non-pregnant subject is used (Panel A) and high percentage of binding of lymphocytes to platelets is observed when serum from a pregnant woman is used (Panel B). In addition to lymphocyte binding of platelets, a difference in the appearance of background is observed. Increased platelet binding to lymphocytes is associated with a clearing up of the background, thus making it appear empty.

Table II shows results of percentage of lymphocyte binding to platelets using sera from non-pregnant women receiving progesterone replacement therapy during the luteal phase or oral contraceptives (estrogen and progesterone). All of the values are within the non-pregnant range demonstrating no effect of these steroids on the results of the PIF assay.

TABLE II

Percentage of lymphocytes binding to platelets in
the lymphocyte/platelet binding assay using sera from
non-pregnant women, receiving estrogen and/or
progesterone therapy.

| Subject | Treatment | % binding |
|---|---|---|
| 1 | Progesterone | 17 |
| 2 | Progesterone | 22 |
| 3 | Progesterone | 32 |
| 4 | Estrogen and progesterone | 30 |

Table III shows the effect of hCG on the results of the lymphocyte/platelet binding assay. No effects on the binding of platelets were found whether hCG was added to the assay mixture alone or premixed with non-pregnant serum.

TABLE III

The effect of human chorionic gonadotropin on the
results of the lymphocyte/platelet binding assay.

| Amount of hCG added to assay | % binding | | | |
|---|---|---|---|---|
| units | Exp 1 | Exp 2 | Exp 3 | Exp 4 |
| 0 | 25 | 19 | 28 | 18 |
| 5 | 25 | 21 | 11 | 20 |
| 10 | 23 | 23 | 9 | 23 |
| 15 (+15 μl serum) | 28 | 20 | 15 | 16 |

Prospective PIF Data

Forty-five women undergoing assisted reproductive technology were prospectively followed. Blood was collected either 4 days after embryo transfer following IVF (in vitro fertilization) or 6 days after insemination, and subjected to the PIF assay. It was later determined whether each patient did or did not become pregnant.

Table IV shows the predictive value with respect to pregnancy in these patients, who were tested blindly.

TABLE IV

| Sensitivity | 88% |
|---|---|
| Specificity | 93% |
| Positive predictive value | 88% |
| Negative predictive value | 93% |

Current Protocol

Obtain 5 ml of blood in blue top tube (sodium citrate) from a healthy O(+) donor. Dilute 1:2 with PBS and isolate lymphocytes by density-gradient technique: Histopaque-1077 (Sigma).

Collect interface, favoring the portion above the interface (for platelets).

Wash ×2 with PBS, 600×g, 8 min.

Resuspend in 1 ml PBS.

Check the number of spontaneous bindings (background). Count % of 1 lymphocyte attached to 3 or more platelets. A good donor has no more than 3–4%.

15 μl of cell suspension +15 μl of heat inactivated test serum (controls: pos(+)=known pregnant woman 1st trimester: neg(−)=healthy nonpregnant female)

incubate for 10 minutes at room temperature add 5 μl T11 monoclonal antibody (Ortho)

incubate for 10 minutes at room temperature add 5 μl Rabbit complement (Sigma)

After 5–10 minutes assess percentage of platelet-bound lymphocytes. double blinded and averaged from the two scorers.

THRESHOLD—8% borderline for positivity (preliminary data)

Preparation of PIF Antibodies

Monoclonal antibodies to PIF are obtained by isolation of proteins constituting PIF by known techniques of chromatography and SDS-PAGE electrophoresis, using the lymphocyte/platelet binding bioassay for identification of fractions, followed by known methods for production and isolation of monoclonal antibodies from hybridomas.

BIBLIOGRAPHY

1. Rolfe B E. Detection of fetal wastage. Fertil Steril. 1982;37:655–701.
2. Smart Y C, Fraser I S, Roberts T K, Clancy R L, Cripps A W. Fertilization and early pregnancy loss in healthy women attempting conception. Clin Reprod Fertil. 1982;1:177–182.
3. Morton H, Hegh V, Clunie G J A. Studies of the rosette inhibition test in pregnant mice: evidence of immunosuppression? Proc R Soc Lond [Biol]. 1976;193:413–417.
4. Chard T. Grudzinskas J G. Early pregnancy factor. Biol Res in Preg. 1987;8:53–56.
5. U.S. Congress, Office of Technology Assessment. Infertility, Medical and Social Choices. DTA BA 358. Washington, D.C.: U.S. Government Printing Office; May 1988.
6. Mosher W D, Pratt W F. Fecundity, infertility and reproductive health in the United States, 1992. Vital and Health Statistics. Series 23, no. 14. National Center for Health Statistics, Public Health Service. Washington, D.C.: U.S. Government Printing Office, 27; 1987.

7. Templeton A A, Penny G C. The incidence of characteristics and prognosis of patents whose infertility is unexplained. Fertil Steril. 1982;37:175.
8. Coulam C B. Evaluation of Immunologic infertility. Am J Reprod Immunol. 1992;27:130–135.
9. Collier M, O'Neill C, Ammit A J, Saunders D M. Biochemical and pharmacological characterization of human embryo-derived activating factor. Hum Reprod. 1988;3:993–998.
10. O'Neill C, Gidley-Baird A A, Amnit A J, Saunders D M. Use of a bioassay for embryo-derived platelet activating factor as a means of assessing quality and pregnancy potential of human embryos. Fertil Steril. 1987;47:967–975.
11. O'Neill C. Gidley-Baird A L, Pike A L, Porter R N, Sinosich M J, Saunders D M. Maternal blood platelet physiology and luteal phase endocrinology as a means of monitoring pre- and postimplantation embryo viability following in vitro fertilization. J Vitro Fertil Embryo Transfer. 1985;2:59–65.
12. O'Neill C, Collier M, Saunders D M. Embryo-derived platelet activating factor: its diagnosis and therapeutic future. Ann N Y Acad Sci. 1988;541:398–403.
13. Smart Y C, Roberts T K, Clancy R L, Cripps A W. Early pregnancy factor: its role in mammalian reproduction— research review. Fertil Steril. 1981;35:397–403.
14. Chen C, Jones W R, Bastin F, Forde C. Monitoring embryos after in vitro fertilization using early pregnancy factor. Ann N Y Acad Sci. 1984;442:420–424.
15. Tinneberg H-R, Staves R P, Semm K. Improvement of the rosette inhibition assay for the detection of early pregnancy factor (EPF) in humans using the monoclonal antibody anti-human-Lyt-3. Am J Reprod Immunol. 1984;5:151–155.
16. Morton H, Rolfe B, Clunie G J A, Anderson M J, Morrison J. An early pregnancy factor detected in human serum by the rosette inhibition test. Lancet. 1977;1:394–399.
17. Quin Z H, Zheng Z Q. Detection of early pregnancy factor in human serum. Am J Reprod Immunol Microbiol. 1987;13:15–19.
18. Hanahan D J. Platelet activating factor: A biologically active phosphoglyceride. Annu Reve Biochem. 1986;SS:483–509.
19. O'Neill C. Partial characterization of the embryo-derived platelet activating factor in mice. J Reprod Fertil. 1985;75:375–380.
20. Battye K M, O'Neill C, Evans G. Production of platelet activating factor by the preimplantation sheep embryo. J Reprod Fertil. 1991;93:507–514.
21. Smart Y C, Fraser I S, Roberts T K, Clancy R L, Cripps A W. Fertilization and early pregnancy loss in healthy women attempting conception. Clin Reprod Fertil. 1982b;1:117–184.
22. Smart Y C, Roberts T K, Fraser I S, Cripps A W, Clancy R L. Validation of the rosette inhibition test for the detection of early pregnancy in women. Fertil Steril. 1982c;37:779–785.
23. Smart Y C, Roberts T K. Rosetta inhibition test: assay for detection of early pregnancy factor. In: Ellendorf F, Koch E (eds.) Early Pregnancy Factors. Perinatology Press, Ithaca, N.Y., pp 105–116; 1985.
24. Whyte A, Heap R B. Early pregnancy factor. Nature. 1983;304:121–122.
25. Thomson A W, Milton J I, Campbell D M, Horne C H W. Rosette inhibition levels during early human gestation. J Reprod Immunol 1980;2:263–266.
26. Cooper D W, Aitken R J. Failure to detect altered rosette inhibition titres in human pregnancy serum. J Reprod Fert. 1981;61:241–244.
27. O'Neill C. Thrombocytopenia is an initial maternal response to fertilization in the mouse. J Reprod Fertil. 1985;73:559–564.
28. Nahas F., Barnea E. Human embrionic origin early pregnancy factor before and after implantation. J Reprod Immunol. 1990;22:105–108.
29. Sanyal M K, Brami C J, Bischof P., Simmons E., Barner E R, Dwyer J M, Naftolin F. Immunoregulatory activity in supernatants from cultures of normal human trophoblast cells of the first trimester. Am J Obstet Gynecol. 1989;161:446–453.

We claim:

1. A method for determining prior to implantation whether fertilization has occurred in a female mammal which comprises:
    (a) withdrawing blood from the mammal about four days after insemination; and
    (b) determining the presence or absence of PIF in said blood; whereby a positive Preimplantation Factor (PIF) assay indicates that fertilization has occurred.

2. A pregnancy test which comprises determining the presence or absence of Preimplantation Factor (PIF) in the blood of a female mammal; whereby a positive PIF assay indicates pregnancy.

3. A method of forecasting spontaneous abortion in a mammal known to be pregnant by having a positive Preimplantation Factor (PIF) assay, which comprises periodically testing for the presence of PIF in the blood of said mammal, whereby if the PIF becomes negative intrauterine demise has occurred or will soon occur.

4. A contraception regimen which comprises:
    a) determining, prior to implantation, by the method of claim 1, whether fertilization has occurred in a female mammal; and
    b) administrating to said mammal an effective amount of an anti-implantation agent.

5. Method according to claim 1, wherein the mammal is a human.

6. Pregnancy test according to claim 2, wherein the mammal is a human.

7. Method according to claim 3, wherein the mammal is a human.

8. An assay for Preimplantation Factor (PIF) in mammalian body fluid which comprises contacting same with monoclonal antibodies to PIF, and determining the amount of PIF, if any, bound to said antibodies.

9. Regimen according claim 4, wherein the mammal is a human.

* * * * *